United States Patent [19]  
Hess et al.

[11] 3,934,027  
[45] Jan. 20, 1976

[54] 18β-GLYCYRRHETINIC ACID AMIDES USEFUL AS ANTIULCER AGENTS

[75] Inventors: Hans-Jurgen E. Hess, Old Lyme; Roger P. Nelson, Waterford, both of Conn.

[73] Assignee: Pfizer Inc., New York, N.Y.

[22] Filed: June 24, 1974

[21] Appl. No.: 482,056

Related U.S. Application Data

[62] Division of Ser. No. 356,774, May 3, 1973, Pat. No. 3,859,328, which is a division of Ser. No. 195,475, Nov. 3, 1971, Pat. No. 3,766,206.

[52] U.S. Cl. ............... 424/309; 424/273; 424/274; 424/311; 424/313; 424/319
[51] Int. Cl.² ........................................ A61K 31/235
[58] Field of Search ............ 356/774; 424/311, 309, 424/313, 319

[56] References Cited
UNITED STATES PATENTS

| | | | |
|---|---|---|---|
| 3,412,084 | 11/1968 | Turner et al. | 260/268 |
| 3,523,942 | 8/1970 | Holden | 260/268 |

*Primary Examiner*—Frederick E. Waddell  
*Attorney, Agent, or Firm*—Francis X. Murphy; Charles J. Knuth; Albert E. Frost

[57] ABSTRACT

Amide derivatives of 18β-glycyrrhetinic acid and its 3-alkanoyl derivatives useful as antiulcer agents wherein the amide is derived from an amino acid.

6 Claims, No Drawings

18 GLYCYRRHETINIC ACID AMIDES USEFUL AS ANTIULCER AGENTS

CROSS REFERENCE TO RELATED APPLICATION

This application is a divisional application of copending application Ser. No. 356,774, filed May 3, 1973 and now U.S. Pat. No. 3,859,328, which in turn is a divisional application of application Ser. No. 195,475, filed Nov. 3, 1971, now U.S. Pat. No. 3,766,206, issued Oct. 16, 1973.

BACKGROUND OF THE INVENTION

This invention relates to novel derivatives of glycyrrhetinic acid and to their use as antiulcer agents. More specifically, it relates to amide derivatives of 18β-glycyrrhetinic acid and its 3-alkanoyl derivatives which are useful antiulcer agents wherein the amide is derived from an amino acid.

Chronic gastric and duodenal ulcers, collectively known as peptic ulcers, are a common affliction for which a variety of treatments have been developed. The treatment depends upon the severity of the ulcer and may range from dietary and medical (drug) treatment to surgery. A wide variety of drugs have been used to treat ulcers, the most recent of which to gain widespread attention is carbenoxolone sodium, the disodium salt of the hemissuccinate of glycyrrhetinic acid. It is reported to prevent formation of and to accelerate healing of gastric ulcers in animals, including humans, ("Carbenoxolone Sodium: A Symposium," J. M. Robson and F. M. Sullivan, Eds., Butterworths, London, 1968). However, its use is accompanied by undesirable aldosterone-like side effects, such as marked antidiuretic and sodium-retaining activity and, oftentimes, potassium loss, such that continued therapy with this agent often leads to hypertension, muscle weakness and, ultimately, congestive heart failure.

Carbenoxolone sodium is almost wholly absorbed in the stomach and is not effective against duodenal ulcers except when administered as a specially formulated capsule which enables its transport to the desired site.

A more effective treatment of peptic ulcers is, therefore, desirable. One which will effectively act upon ulcers in the duodenum, as well as upon gastric ulcers, without the need of special formulation and minimizes the aldosterone-like side effects of carbenoxolone is especially desirable.

Glycyrrhetinic acid, esters, 3-acyloxy derivatives, salts and amides thereof are known to exhibit pharmaceutical properties. British Pat. No. 628,443 (Aug. 14, 1963) reports glycyrrhetinic acid to be an antiinflammatory, analgesic and antipyretic agent. U.S. Pat. No. 3,070,623 (Dec. 25, 1962) described hemi-esters of glycyrrhetinic acid, including the hemisuccinate (also known as carbenoxolone sodium), as anti-inflammatory agents. U.S. Pat. No. 3,070,624 (Dec. 25, 1962) teaches basic esters of the carboxy group at the 20-position of glycyrrhetinic acid which exhibit anti-inflammatory properties and inhibit the action of steroids and steroidal metabolism. Antiinflammatory and analgesic properties are reported for amino acid salts of glycyrrhetinic acid in Japanese Pat. No. 32798/69, published Oct. 27, 1965. French Pat. No. 215 CAM/5544M, published July 19, 1968, discloses hypoglycemic activity for glycyrrhetinic acid and its methyl ester. Salts of glycyrrhetinic acid and its hemi-esters with aluminum, zinc, bismuth and metals of groups II-A and VIII of the Periodic Chart of the Elements are reported in Belgian Pat. No. 628,444, published Feb. 4, 1963, to be of value in treating digestive disorders, such as gastric acidosis, inflammation and ulcers.

Amides of glycyrrhetinic acid and its 3-acyl derivatives useful as anti-inflammatory agents are described in a number of patents. Cyclic amides, e.g., the piperazine, N-acylpiperazides, N-carbalkoxypiperazides, are described in Belgian Pat. No. 753,773, granted July 28, 1969. The N-(lower alkyl)piperazides, piperidide and morpholide are disclosed in Japanese Pat. No. 26,300/67, published Dec. 13, 1967, (C.A. 69, 44067t, 1968). Additionally, simple amides, e.g., the di(lower alkyl)substituted amides, are described in this Japanese Patent. U.S. Pat. No. 3,412,084 (Nov. 19, 1968) teaches alkyl, cycloalkyl, aralkyl and aryl substituted amides of glycyrrhetinic acid as well as heterocyclic amides thereof, all of which are reported to be antiinflammatory agents of low toxicity. Dialkylaminoalkyl substituted amides of glycyrrhetinic acid are described by Adanin et al., Zh. Obshch. Khim. 37, 1063–65 (1967) (C.A. 68, 22087q, 1968). Alkylolamine condensates of glycyrrhetinic acid useful as anti-inflammatory agents in cosmetics are reported in Japanese Pat. No. 8382/67, published Nov. 4, 1967.

A variety of derivatives of glycyrrhetinic acid and 11-deoxoglycyrrhetinic acid are described by Dean et al., J. Pharm. Pharmac. 19, 682–9 (1967); including the hemi-succinates of methyl glycyrrhetinate, glycyrrhetinamide and 11-deoxoglycyrrhetinic acid; the 3-acetyl derivatives of glycyrrhetinamido-ortho- and para-benzoic acids; and N-(glycyrrhetinyl)glycine(-glycyrrhetinuric acid).

Various derivatives of 11-deoxoglycyrrhetinic acids useful as intermediates are described by Ruzicka et al. in Helv. Chim. Acta 20, 1271 (1937) and 22, 197 (1939); Corey et al., J. Am. Chem. Soc. 81, 1745 (1959) and Drefahl et al., Ber. 94, 2015 (1961): the acetyl-, the methyl ester, the acetyl-acid chloride, the acetyl methyl ester, the acetyl azide and the acetyl amide.

Groen et al., Acta. Med. Scand. Suppl. 312, 745–748 (1956) in a comparative study of the pharmacological activity of the adrenocortical steroids and glycyrrhetinic acid noted that in order to retain activity in either class of compounds only a limited degree of structural variation is possible. They noted that "the activity seemed dependent on the presence of an 11-keto group." Vinogradov et al., Khim. v Estestn. Naukaki Sb. 40-6, 1965 (C.A. 65, 6136c, 1966) report the methyl ester of 11-deoxoglycyrrhetinic acid gave rise to a sharp increase in the excretion of water and sodium by the kidneys in dogs. In rats, 11-deoxoglycyrrhetinic relieved the action of deoxycorticosterone.

SUMMARY OF THE INVENTION

It has now been found that 18β-glycyrrhetinic acid amides of the formula below are effective antiulcer agents:

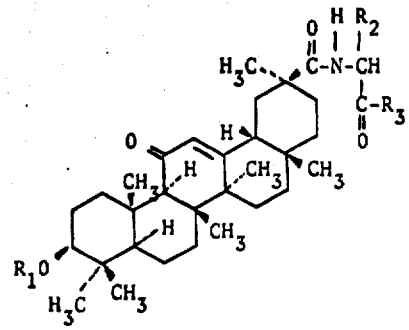

wherein
- $R_1$ is selected from the group consisting of hydrogen, alkanoyl having from 2 to 6 carbon atoms, and ω-carboxyalkanoyl having a total of from 4 to 5 carbon atoms;
- $R_2$ is selected from the group consisting of hydroxymethyl,
  1-hydroxyethyl,
  mercaptomethyl,
  2-methylmercaptoethyl,
  4- (or 5) imidazolylmethyl,
  benzyl,
  4-hydroxybenzyl,
  3,4-dihydroxybenzyl,
  3,5-dibromo-4-hydroxybenzyl,
  carboxy,
  carbalkoxy having from one to four carbon atoms in the alkoxy moiety, ω-carboxyalkyl having from one to two carbon atoms in the alkyl moiety,
  ω-(carbalkoxy)alkyl having from one to four carbon atoms in the alkoxy group and from one to two carbon atoms in the alkyl group,
  ω-aminoalkyl having from two to four carbon atoms in the alkyl moiety,
  3-quanidinopropyl,
  3-ureidopropyl and
  3-indolylmethyl; and
- $R_3$ is selected from the group consisting of hydroxy and alkoxy having from 1 to 4 carbon atoms, and when $R_2$ is ω-carboxyalkyl or ω-(carbalkoxy)alkyl, $R_3$ is also di-(n-propyl)amino.

Also included in this invention are the pharmaceutically-acceptable alkali metal salts (sodium and potassium) of these compounds which contain at least one carboxy group; i.e., those wherein $R_1$ is ω-carboxyalkanoyl, or $R_3$ is hydroxy or $R_2$ is carboxy or ω-carboxyalkyl; and the pharmaceutically-acceptable acid addition salts of those compounds in which the amide moiety has a basic group such as those wherein $R_2$ is ω-aminoalkyl- or 3-quanidinopropyl-. Representative of the acid addition salts are the hydrochloride, hydrobromide, sulfate, phosphate, nitrate, acetate, propionate, butyrate, citrate, gluconate, tartrate, benzoate, succinate, malate, maleate and fumarate.

In addition to the alkali metal salts of those compounds of this invention containing a carboxy group, salts with metals such as the alkaline earth metals, especially calcium and magnesium and with aluminum, zinc and bismuth, and metals of group VIII of the Periodic Chart of the Elements are also included.

DETAILED DESCRIPTION OF THE INVENTION

The novel products of this invention, that is, all compounds of the above formula, are prepared by acylation of the appropriate amino acid $R_2CH(NH_2)COR_3$ reactant with an acid halide (chloride or bromide) of 18β-glycyrrhetinic acid in which the 3-hydroxy group is suitably protected as, for example, by acylation with a monocarboxylic acid, anhydride or acid halide, or with the acid chloride of a dicarboxylic acid half-ester. Protection of the 3-hydroxy group is necessary to permit formation of the acid halide of the glycyrrhetinic acid. The acid halides of the 3-acyl-18β-glycyrrhetinic acids are prepared by treating the 3-acyl-18β-glycyrrhetinic acids with excess thionyl chloride or bromide at from about room temperature to the boiling point of the thionyl halide and, subsequently, removing the excess thionyl halide. The favored acid halides are the acid chlorides since they provide satisfactory yields of desired product. The favored protecting group at the 3-hydroxy group is acetyl since it is easily removed by mild hydrolysis to regenerate the free hydroxy group.

When the amino acid reactant is a basic amino acid, or contains an hydroxy or mercapto group, such group is protected prior to acylation with the 18β-glycyrrhetinic acid halide.

Compounds of the above formula wherein $R_1$ is ω-carboxyalkanoyl are prepared by hydrolysis of an ester of the ω-carboxyalkanoyl group, e.g., an alkyl ester, and preferably a methyl or ethyl ester, by means of lithium iodide in N,N-dimethylformamide at the reflux temperature. This treatment, of course, also hydrolyzes any ester group present in the amide moiety. Alternatively, an ω-carbobenzyloxy alkanoyl derivative can be used in place of an ω-carbalkoxyalkanoyl derivative. The benzyl group is easily removed by catalytic hydrogenation, e.g., with palladium on charcoal. This procedure has the advantage of permitting retention of alkyl ester groups in the amide moiety.

The 3-acyl-18β-glycyrrhetinic acid amides thus produced, in addition to being anti-inflammatory and anti-ulcer agents, serve as intermediates, particularly for the production of half esters with dicarboxylic acids. The 3-hydroxy group produced on hydrolysis is reacylated with an acid anhydride or acid halide of a dicarboxylic acid half ester to produce a compound wherein $R_1$ is ω-carboxyalkanoyl, or an ester thereof.

When the amide moiety contains an amino, hydroxy or mercapto group, such group must first be protected before acylation of the 3-hydroxy group. A suitable and convenient protecting group is the benzyl group since it is easily removed by hydrogenolysis. This group can be present in the $R_2CH(NH_2)COR_3$ reactant or be introduced into the 18β-glycyrrhetinic acid amide.

The compounds described herein are effective anti-ulcer agents via the intraperitoneal and oral routes of administration against gastric and duodenal ulcers. These products not only accelerate healing of such ulcers but also prevent formation of ulcers and decrease gastric acid output in animals, including humans. They can, therefore, be said to be useful for the control of gastric and duodenal ulcers. The incidence of side effects, e.g., aldosterone-like fluid retention and electrolyte disturbances, attendant with the use of many of the compounds of this invention is relatively low and is nonexistent with some of them. Particularly valuable in this respect are N-[3β-hydroxy-11-oxo-18β-olean-12-en-30-oly]phenylalanine; N-[3β-hydroxy-11-oxo-18β-olean-12-en-30-oyl]L-histidine; N-[3β-acetoxy-11-oxo-18β-olean-12-en-30-oyl]L-histidine, methyl ester.

The valuable products of this invention can be administered alone or in combination with a pharmaceutical carrier selected on the basis of the chosen route of administration and standard pharmaceutical practice. For example, they can be administered orally in the form of tablets containing such excipients as polyvinylpyrrolidone, a Carbowax (non-volatile, solid polyethylene glycols available from Carbide and Carbon Chemicals Corporation), especially Carbowax 6000, starch, milk sugar, etc., or in capsules alone or in admixture with the same or equivalent excipients. They may also be administered orally in the form of elixirs or oral suspensions which may contain flavoring or coloring agents or be injected parenterally; that is, for example, intramuscularly or subcutaneously. For parenteral administration, they are best used in the form of a sterile solution which may be either aqueous, such as water, isotonic saline, isotonic dextrose, Ringer's solution; or non-aqueous, such as fatty oils of vegetable origin (cotton seed, peanut oil, corn, sesame) and other non-aqueous vehicles which will not interfere with the therapeutic efficiency of the preparation and are non-toxic in the volume or proportion used (glycerol, propylene glycol, sorbitol). Additionally, compositions suitable for extemporaneous preparation of solutions prior to administration may advantageously be made. Such compositions may include liquid diluents, for example, propylene glycol, diethyl carbonate, glycerol, sorbitol, etc.; buffering agents, as well as local anesthetics and inorganic salts to afford desirable pharmacological properties.

For both oral and intraperitoneal administration, a dosage range of from about 150 mg. to about 300 mg. per day is effective. The dosage level can, with careful supervision, range up to as high as about two grams per day. Propylene glycol is a suitable and convenient carrier or diluent for intraperitoneal use. Carbowax 6000 is a favored excipient for oral use. Compositions containing from about 50% to about 90% by weight of polyvinylpyrrolidone or Carbowax 6000 are especially effective for oral administration. Higher or lower amounts of excipient can, of course, be used but appear to offer no advantages over these proportions. For intraperitoneal use, the polyvinylpyrrolidone formulations are suspended in carriers such as water, or in saline solution containing 1% carboxymethylcellulose and 0.1% Tween 80 (polyoxyethylene ethers of partial esters of fatty acids and hexitol anhydrides derived from sorbitol, available from Atlas Chemical Industries, Inc.). The water-soluble products of this invention are conveniently administered in water solution.

The effectiveness of the products of this invention as antiulcer agents is determined by the stressed rat assay as follows:

Cold-Restraint Stressed Rat

Non-fasted female rats (Charles River C-D strain) weighing 70–140 gms. are administered the drug or carrier (control animals) intraperitoneally (in saline solution containing 1% carboxymethylcellulose and 0.1% Tween 80) or orally (in water) three hours before being lightly anesthetized with ether and taped in the supine position to individual sheets of plexiglass. After recovery from the anesthesia, the restrained animals are positioned horizontally in a refrigerator maintained at 10°–12° C. and 3 hours later sacrificed by cervical dislocation. The abdomen of each rat is opened, the pylorus clamped, the stomach inflated with saline via an oral tube, the esophagus clamped and the stomach excised. The stomachs are placed in a 0.4% formaldehyde solution for approximately 30 seconds to harden the outer layers and facilitate examination. Each stomach is then cut open along the greater curvature and the glandular portion (hind stomach) examined for damage. The number of gastric erosions, their severity and the color of the stomachs is recorded. The Mann-Whitney-Wilcoxon rank sum test is used to compare the median number of gastric erosions in the control group with the median number of gastric erosions in each drug-treated group to determine if they are statistically different. (Dixon et al., "Introduction to Statistical Analysis," 3rd Ed., McGraw-Hill Book Company, New York, pp. 344–347, 1969.)

The effect of the products of this invention on renal excretion of water and electrolytes in rats is determined in the following manner:

Rat Diuretic Assay

The water load (25 ml./kg.) or water load-containing drug is administered orally to each of three groups of two rats. Urine is collected for 5 hours and the samples from each group are analyzed by standard flame photometric techniques for sodium and potassium content. Urinary volume (ml./kg./5 hr.), sodium excreted (mEq./kg./5 hr.), potassium excreted (mEq./kg./5 hr.), and the sodium-potassium ratio is calculated for each group. The sodium/potassium ratio is modified by raising the denominator to the 1.3 power to yield a measure which is independent of the sodium/volume and potassium/volume ratios. Dose-response regression lines are calculated by combining data from all trials using water controls as zero dose.

In water loaded rats, with increasing dose, carbenoxolone causes a moderate decrease in urinary volume and sodium, a marked decrease in the sodium/potassium ratio and a marked increase in potassium concentration, a slight but non-significant increase in urinary potassium and a decrease in urinary sodium concentration.

Their effect on gastric acid output in pylorus-ligated (i.e., Shay) rats is determined by the following procedure.

Shay Rat

Forty-eight hours before surgery female rats (Charles River C-D strain; 100–140 gms.) are individually caged and taken off normal food. Each animal is given two sugar cubes and water ad libitum to effect emptying of the stomach. Drug or carrier is administered intraperitoneally and three hours later, under ether anesthesia, the abdomen is shaved and opened along the linea alba. After exposing and ligating the pylorus, the incision is closed and the animal is returned to its cage and allowed to regain consciousness. Three hours later the animal is sacrificed by cervical dislocation, the abdomen reopened, the distal esophagus clamped, and the stomach excised. The stomach is cut open and the contents washed into a beaker with one ml. of deionized water. The volume of gastric juice is recorded following centrifugation. Excessively dirty (greater than 0.5 ml. of solids) or bloody samples are discarded. The acidity of one ml. of gastric juice is determined by titration with a standardized NaOH (0.1N) solution using phenolphthalein as an indicator and total acid output ($\mu$eqH$^+$/100 gms. body weight/3 hours) is calculated. A non-paired t test is used to compare the means of the control and tested groups. (Dixon et al., Technometrics, X, 83–98, 1968.) Carbenoxolone at 40 mg./kg. body weight consistently reduced gastric acid output in the three-hour Shay rat. At 80 mg./kg., carbenoxolone significantly decreased acid output in the Shay rat.

By means of the above test procedures N-[3$\beta$-hydroxy-11-oxo-18$\beta$-olean-12-en-30-oyl]phenylalanine; N-[3β-hydroxy-11-oxo-18β-olean-12-en-30-oyl]-L-histidine and N-[3β-acetoxy-11-oxo-18β-olean-12-en-30-oyl]L-histidine, methyl ester are found to exhibit significant antiulcer activity in rats at 40 mg./kg. of body weight via the intraperitoneal route of administration. None of the above-named compounds exhibit antidiuretic activity in rats at 80 mg./kg. of body weight when administered intraperitoneally. The first named compound exhibited no antisecretory activity in the Shay rat at 40 mg./kg. of body weight when administered intraperitoneally in propylene glycol. The second named compound showed no antisecretory activity when given intravenously at 50 mg./kg. of body weight. The last named compound exhibited mild, if any, antisecretory activity in the Shay rat which is not dose related.

EXAMPLE I

N-[3β-Hydroxy-11-Oxo-18β-Olean-12-En-30-Oyl]-L-Methionine

A. 3β-Acetoxy-11-Oxo-18β-Olean-12-En-30-Oic Acid

A suspension of 100 g. (0.210 mole) of 18β-glycyrrhetinic acid and 24.8 g. (0.360 mole) of acetylchloride in 400 ml. of pyridine is stirred at room temperature for 22 hours. The reaction mixture is made acidic with 10% hydrochloric acid and the resulting solid filtered, washed with water and recrystallized from ethanol to give 88.9 g., 82.6% yield of product; m.p. 318°–320.5° C. (Beaton et al., J. Chem. Soc., 2417, (1956) report m.p. 310°–312° C.)

B. 3β-Acetoxy-11-Oxo-18β-Olean-12-En-30-Oyl Chloride

A solution of 15.0 g. (0.0293 mole) of acetate (A) in 150 ml. of thionyl chloride is heated at reflux for one hour and the reaction mixture then concentrated to dryness under vacuum. Methylene chloride is added to the residue and the mixture again concentrated to dryness. The latter procedure is repeated twice more. The resulting solid is recrystallized from methylene chloride/hexane to give 8.89 g., 57.3% yield of acid chloride; m.p. 281°–283° C. (Drefahl et al., Ber. 94, 2015 (1961) report m.p. 295° C.)

C. N-[3β-Hydroxy-11-Oxo-18β-Olean-12-En-30-Oyl]-L-Methionine

To a solution of 6.00 g. (0.0113 mole) of acid chloride (B) in 120 ml. of methylene chloride is added 2.25 g. (0.0113 mole) of L-methionine methyl ester hydrochloride and 2.29 g. (0.0226 mole) of dry triethylamine. The reaction mixture is stirred for 72 hours at room temperature and then treated with water and extracted with methylene chloride. The extract is dried over sodium sulfate, decolorized and filtered. Concentration of the filtrate gives a solid which is recrystallized from acetone, yielding 6.97 g. (93.9%) of crude product; m.p. 189°–190° C. Six grams of the solid is stirred in 270 ml. of 10% methanolic-potassium hydroxide for 2 hours. The reaction mixture is then acidified with 10% HCl and extracted with methylene chloride. The combined extracts are concentrated and recrystallized from isopropyl ether-ethyl acetate to give 4.07 g., 76.6% yield of product; m.p. 268°–270° C. A small quantity, 0.500 g. (0.000831 mole) of the purified methionine derivative is treated with 0.378 g. (0.000831 mole) of 2.419N sodium hydroxide and the white paste dried to give the white crystalline sodium salt of the title product.

EXAMPLE II

N-[3β-Acetoxy-11-Oxo-18β-Olean-12-En-30-Oyl]L-Histidine, Methyl Ester

To a suspension of 2.73 g. (0.0113 mole) of L-histidine methyl ester dihydrochloride, 4.39 g. (0.0339 mole) of N,N-diisopropylethylamine and 20 ml. of methylene chloride is added 6.00 g. (0.0113 mole) of 3β-acetoxy-11-oxo-18β-olean-12-en-30-oyl chloride in 55 ml. of methylene chloride over a 30-minute period. The hazy mixture is stirred at room temperature for 67 hours and then washed with water, dried over sodium sulfate and treated with activated charcoal. Concentration of the resulting solution gives an oil which is dissolved in methanol and allowed to crystallize. The filtered solid, 5.49 g., 73.2% yield; m.p. 224°–226° C., is recrystallized from methanol to give 4.42 g. of purified product; m.p. 227.5°–229° C.

In like manner, corresponding molar amounts of citrulline methyl ester, cysteine ethyl ester, lysine methyl ester, and methyl α,γ-diaminobutyrate react with the acid chloride to afford N-[3β-acetoxy-11-oxo-18β-olean-12-en-30-oyl]citrulline, methyl ester; N-[3β-acetoxy-11-oxo-18β-olean-12-en-30-oyl]cysteine, ethyl ester; and N-[3β-acetoxy-11-oxo-18β-olean-12-en-30-oyl]-D-histidine, methyl ester. Moreover, when 3β-acetoxy-11-oxo-18β-olean-12-en-30-oyl chloride is replaced by the corresponding 3β-propionyloxy-, 3β-butyryloxy and 3β-n-hexoxy derivatives in this procedure, the corresponding 3β-acyl derivatives of the above-named compounds are obtained.

EXAMPLE III

N-[3β-Hydroxy-11-Oxo-18β-Olean-12-En-30-Oyl]-L-Histidine

A mixture of 3.00 g. (0.00453 mole) of the histidine ester derivative of Example II and 140 ml. of 10% KOH/MeOH is stirred at room temperature for 3 hours. The reaction mixture is made acidic with 10% hydrochloric acid and then extracted with methylene chloride. A portion of the product is filtered from the aqueous layer and the aqueous filtrate saturated with sodium chloride and extracted with chloroform. The combined extracts are concentrated to dryness and combined with the initially filtered solid to give 2.82 g., 96.6% yield, of desired product as the hydrochloride salt; m.p. 265°–269° C. Recrystallization from isopropyl alcohol-petroleum ether gives material melting at 257°–259° C. The sodium salt is prepared by treating the solid with two equivalents of aqueous sodium hydroxide according to the procedure of Example I-C.

In the same mannerr, the remaining products of Example II are hydrolyzed to give N-[3β-hydroxy-11-oxo-18β-olean-12-en-30-oyl]citrulline; and N-[3β-hydroxy-11-oxo-18β-olean-12-en-30-oyl]cysteine; and N-[3β-hydroxy-11-oxo-18β-olean-12-en-30-oyl]-D-histidine which are converted to their sodium salts by the procedure of Example I-C.

EXAMPLE IV

N-[3β-Hydroxy-11-Oxo-18β-Olean-12-En-30-Oyl]-Phenylalanine

To a suspension of 1.62 g. (0.0075 mole) of phenylalanine methyl ester hydrochloride, 4.00 g. (0.00754 mole) of the acid chloride of Example I-B and 20 ml. of methylene chloride is added 1.95 g. of N,N-diisopropylethylamine in 20 ml of methylene chloride over a 2-hour period. The reaction mixture is stirred at room temperature for 67 hours and, subsequently, washed with 10% hydrochloric acid and water. The organic extracts are treated with activated charcoal, dried over sodium sulfate, and concentrated to an oil which solidifies on treatment with acetone, giving 4.51 g., 88.7% yield of N-[3β-acetoxy-11-oxo-18β-olean-12-en-30-oyl]phenylalanine, methyl ester; foams at 150° C., resolidifies and melts at 210°-212° C.

The phenylalanine methyl ester derivative, 3.00 g. (0.00445 mole), is treated with 151 ml. of 10% methanolic-potassium hydroxide for 5 hours at room temperature. The reaction mixture is acidified with 10% hydrochloric acid and the aqueous layer extracted with methylene chloride. The combined organic extracts are decolorized with activated charcoal and filtered through diatomaceous earth. Concentration of the filtrate gives 2.39 g. of crude hydrolysis product; m.p.: foams at 155°-180° C. and melts at 247°-254° C. Recrystallization of the crude from ether-chloroform gives 1.57 g. (57.3% yield) of the title product; m.p. 252.5°-253.5° C. The sodium salt is prepared according to Example I-C using one equivalent of sodium hydroxide.

In the same manner, but using corresponding molar amounts of 3β-propionyloxy- and 3β-valeryloxy-11-oxo-18β-olean-12-en-30-oyl chlorides in place of the 3β-acetoxy derivative provides N-[3β-propionyloxy-11-oxo-18β-olean-12-en-30-oyl]phenylalanine, methyl ester and N-[3β-valeryloxy-11-oxo-18β-olean-12-en-30-oyl]phenylalanine, methyl ester which are subsequently hydrolyzed to the title product by the above procedure.

EXAMPLE V

N-[3 β- Hydroxy-11-Oxo-18β-Olean-12-En-30-Oyl]-L-Tryptophan

To a solution of 2.28 g. (0.00895 mole) of L-tryptophan methyl ester hydrochloride and 2.14 g. (0.0166 mole) of N,N-diisopropylethylamine in 60 ml. of methylene chloride is added a solution of 4.00 g. (0.00759 mole) of the acid chloride of Example I-B in 30 ml. of methylene chloride over a 2-hour period. The mixture is stirred at ambient temperature for 19.5 hours and then washed with 10% hydrochloric acid and the aqueous layer extracted with methylene chloride. The combined organic extracts are dried over sodium sulfate and decolorized. The filtrate is concentrated to a yellow solid which is recrystallized from methanol to give 4.04 g., 75% yield of the 3β-acetoxy derivative of the product; m.p. 252°-253.5°C. The solid, 2.5 g. (0.00351 mole) is treated with 110 ml. of 10% KOH/MeOH for 4 hours. The reaction mixture is acidified with 10% hydrochloric acid and the aqueous layer extracted with methylene chloride. The combined extracts are decolorized, filtered and concentrated to give an oil which yields, upon treatment with acetone, 1.63 g. (71.2%) of the product; m.p. 285°-285.5° C. Its sodium salt is prepared using one equivalent sodium hydroxide as described in Example I-C.

In like manner, the n-butyl ester of L-tryptophan hydrochloride reacts with 3β-butyryloxy-11-oxo-18β-olean-12-en-3-oyl chloride to provide N-[3β-butyryloxy-11-oxo-18β-olean-12-en-30-oyl]-L-tryptophan, n-butyl ester which is hydrolyzed by the above procedure to give the title product.

EXAMPLE VI

N-[3β-Hydroxy-11-Oxo-18β-Olean-12-En-30-Oyl]-L--L-Tyrosine

To a solution of 2.07 g. (0.00895 mole) of L-tyrosine methyl ester hydrochloride in 30 ml. of methylene chloride is added simultaneously a solution of 4.00 g. (0.00754 mole) of the acid chloride of Example I-B in 30 ml. of methylene chloride, and a solution of 2.14 g. (0.0165 mole) of N,N-diisopropylethylamine in 30 ml. of methylene chloride over a 2-hour period. The reaction mixture is stirred for 18.5 hours, washed with 10% hydrochloric acid and the aqueous layer extracted with methylene chloride. The combined extracts are washed with water, dried over sodium sulfate, and treated with activated charcoal. The filtrate is concentrated to give a yellow solid which is recrystallized from methanol and treated with hot ether to give 3.44 g., 66.5% of the 3β-acetoxy derivative of the product; m.p. 269°-271° C. The acetoxy derivative, 2.40 g. (0.00348 mole) is stirred in 108 ml. of 10% KOH/MeOH for 3.5 hours at room temperature. The reaction mixture is made acid with 10% hydrochloric acid and the aqueous layer extracted with methylene chloride. The combined extracts are decolorized and concentrated to dryness. The solid residue is treated with hot acetone to give 0.949 g. (43% yield) of crystalline product; m.p. 273°-273.5° C. The disodium salt is prepared using two equivalents of sodium hydroxide according to the procedure of Example I-C.

When D-tyrosine and D,L-tyrosine are used in this procedure, the corresponding D- and D,L-amide derivatives are produced.

In the same manner, 3β-(n-hexanoyloxy)-11-oxo-18β-olean-12-en-30-oyl chloride and dibromotyrosine ethyl ester react to give N-[3β-hydroxy-11-oxo- 18β-olean-12-en-30-oyl]dibromotyrosine and its sodium salt; 3β-propionyloxy-11-oxo-18β-olean-12-en-30-oyl chloride and dihydroxyphenylalanine methyl ester react to provide N-[3β-hydroxy-11-oxo-18β-olean-12-en-30-oyl]dihydroxyphenylalanine and its sodium salt; and threonine ethyl ester and 3β-acetoxy-11-oxo-18β-olean-12-en-30-oyl chloride react to give N-[3β-hydroxy-11-oxo-18β-olean-12-en-30-oyl]threonine and its sodium salt.

EXAMPLE VII

N-[3β-Hydroxy-11-Oxo-18β-Olean-12-En-30-Oyl-]Amino Malonic Acid

To a solution of 4.00 g. (0.00753 mole) of the acid chloride of Example I-B and 2.92 g. (0.0226 mole) of N,N-diisopropylethylamine in 50 ml. of methylene chloride is added portionwise 1.75 g. (0.00828 mole) of diethylaminomalonate hydrochloride over a period of one hour. The mixture is stirred at room temperature for 66.5 hours, washed with 10% hydrochloric acid and the aqueous layer extracted with methylene chloride. The organic extracts are washed with water, treated with charcoal and dried over sodium sulfate. Concentration of the filtrate gives a solid which is recrystallized from methanol; yield 3.038 g., 60.0% of the 3β-acetoxy derivative of the desired amide; m.p. 186°-187°C. Two grams (0.00299 mole) of the solid is treated with 292 ml. of 10% KOH/MeOH for 5.5 hours at room temperature. The reaction mixture is concentrated to dryness in vacuo, cooled and acidified with 10% hydrochloric acid. The resulting precipitate is filtered and dissolved in acetone at room temperature. Precipitation of the product is achieved by the addition of petroleum ether to give 1.26 g., 73.6% of product; m.p. 272°–274°C. An analytical sample, m.p. 281°–281.5°C., is prepared by recrystallization from acetone. The disodium salt is prepared (using two equivalents of sodium hydroxide) by the procedure of Example I-C.

In like manner, but using dimethyl aspartate and dimethyl glutamate in place of diethyl malonate affords the corresponding N-[3$\beta$-hydroxy-11-oxo-18$\beta$-olean-12-en-30-oyl]aspartic acid and glutamic acid compounds which are converted to their disodium salts according to Example I-C.

EXAMPLE VIII

N-(3$\beta$-Hydroxy-11-Oxo-18$\beta$-Olean-12-En-30-Oyl)Serine

To a mixture of 4.00 g. (0.00838 mole) of 18$\beta$-glycyrrhetinic acid and 1.31 g. (0.00838 mole) of L-serine methyl ester hydrochloride in 50 ml. of methylene chloride is added, consecutively, solutions of 0.848 g. (0.00838 mole) of triethylamine in 5 ml. of methylene chloride and 1.74 g. (0.00838 mole) of N,N'-dicyclohexylcarbodiimide in 45 ml. of methylene chloride. The reaction mixture is stirred at 10°C. for 7.5 hours and then at room temperature for 60 hours. The precipitated N,N'-dicyclohexylurea is filtered off and the filtrate concentrated to dryness. The residue is treated with hot petroleum ether and filtered. The solid is dissolved in methylene chloride and washed successively with 10% hydrochloric acid, 10% sodium bicarbonate and water. The methylene chloride solution is dried over sodium sulfate, decolorized with activated charcoal and concentrated to a white solid. The solid is recrystallized from ethyl acetate to give 2.29 g. (46.9%) of the intermediate methyl ester, m.p. 246°–248°C.

The methyl ester 1.92 g. (0.00332 mole) is stirred at room temperature in 110 ml. of 10% methanolic-potassium hydroxide for one hour. The reaction mixture is acidified with 10% hydrochloric acid, extracted with methylene chloride and the combined extracts washed with water and concentrated to yield 1.91 g. (~100%) of the title product; m.p. 191°–194°C. (with bubbling). It is converted to its sodium salt by treatment with one equivalent of sodium hydroxide according to the procedure of Example I-C.

Similarly, substitution of L-serine methyl ester of the above procedure by a corresponding molar amount of threonine isopropyl ester affords the intermediate N-(3$\beta$-acetoxy-11-oxo-18$\beta$-olean-12-en-30-oyl)threonine, isopropyl ester which is hydrolyzed to the N-(3$\beta$-hydroxy-11-oxo-18$\beta$-olean-12-en-30-oyl)threonine.

EXAMPLE IX

N-[3$\beta$-Hydroxy-11-Oxo-18$\beta$-Olean-12-En-30-Oyl]-N,N-Di-n-Propylisoglutamine To a solution of 3.00 g. (0.00565 mole) of 3$\beta$-acetoxy-11-oxo-18$\beta$-olean-12-en-30-oyl chloride and 1.74 g. (0.0062 mole) of $\gamma$-methyl N,N-di-n-propylisoglutamine in 30 ml. of methylene chloride is added to 1.61 g. (0.0124 mole) of N,N-diisopropylethylamine in 15 ml. of methylene chloride dropwise over a period of 2 hours. The reaction mixture is stirred at room temperature for 72 hours and then washed with 10% hydrochloric acid and water. The organic layer is dried over sodium sulfate, treated with activated charcoal and concentrated to an oil in vacuo. The oil crystallizes following treatment with ethyl acetate to give 3.24 g. of crude product. The crude product 2.5 g. (0.00338 mole) is stirred in 110 ml. of 10% methanolic-potassium hydroxide for 3.5 hours. The mixture is acidified with 10% hydrochloric acid and extracted with methylene chloride. The extracts are combined, dried over sodium sulfate, treated with activated charcoal and filtered. The filtrate is concentrated to dryness and the residue recrystallized from ethanol to yield 1.14 g. (49.6% yield) of the title product; m.p. 269°–270°C.

Preparation of $\gamma$-methyl-N,N-di-n-propylisoglutamine

To a chilled suspension of 10.0 g. (0.0338 mole) of $\gamma$-methyl N-carbobenzyloxy-L-glutamate in 60 ml. of ether is added 6.80 g. (0.0360 mole) of phosphorous pentachloride and the reaction mixture stirred at 10°C. for 20 minutes. The liquid phase is decanted from the unreacted phosphorous pentachloride and the decanted solution treated with petroleum ether. Cooling of the mixture (dry ice-acetone bath) gives an oily precipitate which crystallizes upon being washed with petroleum ether giving 10.6 g. (~100%) of the acid chloride of $\gamma$-methyl N-carbobenzyloxy-L-glutamate.

Di-n-propylamine (10.2 ml., 0.0744 mole) is added dropwise to a chilled (in ice water) solution of 10.6 g. (0.0338 mole) of the acid chloride in 75 ml. of ether. The reaction mixture is stirred at room temperature for 16 hours, the precipitate filtered and the filtrate washed with water. The ether layer is concentrated to give 7.20 g. (56% yield) of oily amide. To a solution of 7.20 g. (0.019 mole) of the amide in 13.8 ml. of glacial acetic acid is added a solution of 5.23 g. of hydrogen bromide in 13.8 ml. of glacial acetic acid. The solution is stirred at room temperature for 1.5 hours and then concentrated to an oil under reduced pressure at 40°C. The oily residue is dissolved in water and extracted with ether. The aqueous phase is made basic with dicyclohexylamine and the resulting salt filtered and washed with ether. The aqueous filtrate and ether wash are combined and filtered to remove additional salt. The aqueous phase is separated and extracted with ether. The combined ether extracts are dried over sodium sulfate and treated with hydrogen chloride. The solution is concentrated to dryness and the residue recrystallized twice from ethyl acetate to give 2.53 g. (47.6%) of $\gamma$-methyl N,N-di-n-propylisoglutamine; m.p. 134°–135°C.

In the same manner, but using $\beta$-ethyl N,N-di-n-propylisoasparagine as the amino acid reactant in the above procedure affords N-(3$\beta$-hydroxy-11-oxo-18$\beta$-olean-12-en-30-oyl)-N,N-di-n-propylisoasparagine.

The $\beta$-ethyl N,N-di-n-propylisoasparagine reactant is prepared by the procedure set forth above for $\gamma$-methyl N,N-di-n-propylisoglutamine.

EXAMPLE X

Hemisuccinate of N-[3$\beta$-Hydroxy-11-Oxo-18$\beta$-Olean-12-En-30-Oyl]-Phenylalanine A. 3$\beta$-($\beta$-Carbomethoxypropionyloxy)-11-oxo-18$\beta$-olean-12-en-30-oic acid A solution of 18$\beta$-glycyrrhetinic acid (5.0 g.) in pyridine (20 ml.) is treated with a solution of $\beta$-carbomethoxypropionyl chloride (3 ml.) in pyridine (50 ml.). The reaction mixture is allowed to stand for 4 days and then poured into water (100 ml.). The product is extracted with ether (3 × 250 ml.), the combined ethereal extracts dried (MgSO$_4$) and evaporated under reduced pressure. The residue is recrystallized from methanol-water.

Similarly, the corresponding 3β-(γ-carbomethoxybutyryloxy) derivative is prepared substituting γ-carbomethoxybutyrylchloride for β-carbomethoxypropionyl chloride.

A solution of 3β-(β-carbomethoxypropionyloxy)-11-oxo-18β-olean-12-en-30-oyl chloride (11.54 g., 0.02 M, prepared from the precursor acid by the procedure of Example I-B) in methylene chloride (75 ml.) is added dropwise, with stirring, to a solution of phenylalanine methyl ester (2.0 M) in methylene chloride (50 ml.) and the mixture stirred at room temperature for 17 hours. It is then washed successively with 10% hydrochloric acid, sodium bicarbonate solution and water, and then dried (Na$_2$SO$_4$). The product is recovered by removal of the solvent under reduced pressure.

C. Hydrolysis of the ester is accomplished by treating a solution of the ester in N,N-dimethylformamide (15 ml./1.0 mM of ester) with lithium iodide (10 g./1.0 mM of ester) under reflux for 12 hours. The reaction mixture is cooled, poured into water and the product recovered by filtration, if solid, or by extraction with methylene chloride.

In this manner, the hemisuccinate and hemiglutarate esters of the amides of Examples I-IX derived from amino acids having one amino and one acid group are prepared by substituting the appropriate 3β-carbomethoxyalkanoyloxy-18β-glycyrrhetinic acid chloride for the 3β-alkanoyloxy-18β-glycyrrhetinic acid chloride of the Examples.

EXAMPLE XI

N-[3β-(β-Carbomethoxypropionyloxy)-11-Oxo-18β-Olean-12-En-30-Oyl]Serine, Methyl Ester A solution of 3β-(β-carbomethoxypropionyloxy)-11-oxo-18β-olean-12-en-30-oyl chloride (11.54 g., 0.02 M), methyl ester of the hemisuccinate of 18β-glycyrrhetinic acid chloride, in methylene chloride (75 ml.) is added dropwise to a solution of serine methyl ester (2.38 g., 0.02 M) and N,N-diisopropylethylamine (2.58 g., 0.02 M) in methylene chloride (150 ml.). The reaction mixture is stirred for five days at room temperature and then washed with water, decolorized with activated charcoal and dried over magnesium sulfate. Concentration of the solution affords the product.

The dimethyl ester product thus prepared (0.659 g., 1 mM) in N,N-dimethylformamide (75 ml.) is treated with anhydrous lithium iodide (10 g.) and the solution heated at reflux for 12 hours. The reaction mixture is cooled, poured into water, and the product recovered by filtration or by extraction with methylene chloride.

Repetition of this procedure but using 3β-(γ-carbomethoxybutyryloxy)-11-oxo-18β-olean-12-en-30-oyl chloride as the acylating agent provides N-[3β-(γ-carbomethoxybutyryloxy)-11-oxo-18β-olean-12-en-30-oyl]serine, methyl ester which is hydrolyzed in like manner to the corresponding product N-[3β-(γ-carboxybutyryloxy)-11-oxo-18β-olean-12-en-30-oyl]serine.

EXAMPLE XII

N-[3β-Carboxypropionyloxy)-11-Oxo-18β-Olean-12-En-30-Oyl]Lysine

The procedure of Example XI is repeated but using the ε-carbobenzoxy derivative of lysine methyl ester in place of serine methyl ester. The product thus obtained is taken up in ethanol and treated with hydrogen in the presence of 5% palladium on charcoal to remove the protective carbobenzoxy group. Filtration of the catalyst followed by removal of the solvent gives the methyl ester of the hemisuccinate.

Hydrolysis of the dimethyl ester according to the procedure of Example XI produces the title product.

In the same manner, but using the appropriate 3β-alkanoyloxy-11-oxo-18β-olean-12-en-30-oyl chloride the acetyl-, butyryl- and n-hexanoyl derivatives of N-[3β-hydroxy-11-oxo-18β-olean-12-en-30-oyl]lysine methyl ester are prepared. The products are subsequently hydrolyzed to provide the free acid derivative by the procedure of Example I-C.

EXAMPLE XIII

N-[3β-(β-Carboxypropionyloxy)-11-Oxo-18β-Olean-12-En-30-Oyl]Aspartic Acid, Methyl Ester Following the procedure of Example XI, methyl β-amino-β-carbobenzoxy-propionate is treated with 3β-(β-carbobenzoxypropionyloxy)-11-oxo-18β-olean-12-en-30-oyl, prepared by the procedure of Example I-B, to give the benzyl ester of the title product.

The benzyl group is removed using hydrogen, 5% palladium on carbon in ethanol according to Example XII to give the title product.

Repetition of this procedure but using methyl γ-amino-γ-carbobenzoxybutyrate in place of methyl β-amino-β-carbobenzoxy butyrate produces the corresponding 3β-(γ-carboxybutyryloxy) derivative.

In the same manner, but using 3β-propionyloxy-11-oxo-18β-olean-12-en-30-oyl chloride as acylating agent affords N-[3β-propionyloxy-11-oxo-18β-olean-12-en-30-oyl]aspartic acid methyl ester. Hydrolysis of the methyl ester using methanolic-potassium hydroxide as in Example I-C converts the methyl ester to the acid.

EXAMPLE XIV

N-[3β-(β-Carboxypropionyloxy)-11-Oxo-18β-Olean-12-En-30-Oyl]Cysteine

The procedure of Example XI is repeated but using the methyl ester of S-benzylcysteine in place of serine methyl ester. The N-[3β-(β-carbomethoxypropionyloxy)-11-oxo-18β-olean-12-en-30-oyl]-S-benzylcysteine, methyl ester thus produced is hydrolyzed by the procedure of Example XII to the corresponding acid derivative.

Debenzylation is accomplished by treatment with hydrogen in the presence of Pd/C according to Example XII to give the title product.

Repetition of this procedure using 3β-(γ-carbomethoxy butyryloxy)-11-oxo-18β-olean-12-en-30-oyl chloride as acylating agent provides the hemiglutarate of the title compound.

EXAMPLE XV

N-[3β-(β-Carboxypropionyloxy)-11-Oxo-18β-Olean-12-En-30-Oyl]Arginine

This product is prepared from nitroarginine methyl ester hydrochloride and the methyl ester of the hemisuccinate of 18β-glycyrrhetinic acid chloride by the procedure of Example XI. The N-[3β-(β-carbomethoxypropionyloxy)-11-oxo-18β-olean-12-en-30-oyl]nitroarginine, methyl ester thus produced is converted to the corresponding arginine methyl ester by reaction with hydrogen and Pd/C as described in Example XII.

Hydrolysis of the dimethyl ester with lithium iodide according to the procedure of Example XI affords the title product.

In like manner, the hemiglutarate of the title product is prepared using the methyl ester of the hemiglutarate of 18β-glycyrrhetinic acid chloride. When the acetate of acetyl 18β-glycyrrhetinic acid chloride is used as acylating agent, the product is N-[3β-acetoxye11-oxo-18β-olean-12-en-30-oyl]nitroarginine methyl ester. Hydrogenation and hydrolysis of this product afford N-[3β-hydroxy-11-oxo-18β-olean-12-en-30-oyl]arginine.

EXAMPLE XVI

Acid Addition Salt Formation

The appropriate 18β-glycyrrhetinamide which contains a basic group is dissolved in a suitable solvent, e.g., chloroform, methylene chloride, ethanol, and an excess of the appropriate acid added to the solution. The product, if insoluble in the solvent, is recovered by filtration. The product, if soluble in the solvent, is recovered by addition of a non-solvent for the salt, e.g., ether, or by evaporation of the solvent under reduced pressure.

In this manner, the hydrochloride, hydrobromide, tartrate, citrate, acetate, propionate, butyrate, gluconate, benzoate, succinate, malate, maleate, fumarate, nitrate, sulfate and oxalate salts of the products of the preceding examples which contain a basic group are prepared.

EXAMPLE XVII

Metal Salt Formation

A mixture (solution or suspension) of the appropriate 18β-glycyrrhetinamide compound in water is treated with one equivalent of the appropriate metal hydroxide for each carboxy group present. The mixture is stirred at room temperature until reaction is complete and the salt recovered by removal of the water, e.g., by freeze-drying.

In this manner, the sodium and potassium salts of those compounds of the preceding examples having at least one carboxy group are prepared.

PREPARATION A

3β-Alkanoyloxy-11-Oxo-18β-Olean-12-En-30-Oic Acids (via Acid Chlorides)

The procedure of Example I-A is repeated but using the appropriate acid chloride in place of acetyl chloride to give the following 3β-alkanoyl derivatives of 18β-glycyrrhetinic acid:
propionyl
butyryl
valeryl
caproyl

PREPARATION B

3β-Acetoxy-11-Oxo-18β-Olean-12-En-30-Oic Acids (via Acid Anhydrides)

To a solution of 56.5 g. (0.120 M) of glycyrrhetinic acid in 615 ml. of pyridine is added 615 ml. of acetic anhydride. The reaction is refluxed for 1 hour, cooled and stirred at room temperature for 23 hours. It is acidified with 10% hydrochloric acid and the resulting precipitate filtered and dissolved in chloroform. The chloroform solution is washed with water, dried over sodium sulfate and treated with activated charcoal. Concentration of the solution gives a solid which is recrystallized from methanol-chloroform.

Similarly, the propionyl and butyryl derivatives are prepared from propionic and butyric acid anhydrides.

PREPARATION C

3β-Alkanoyloxy-11-Oxo-18β-Olean-12-En-30-Oyl Chlorides

The 3β-alkanoyl derivatives of preparations A and B are converted to their acid chlorides by the procedure of Example I-B.

PREPARATION D

3β-(γ-Carbomethoxybutyryloxy)-11-Oxo-18β-Olean-12-En-30-Oyl Chloride

A solution of 18β-glycyrrhetinic acid (51 g.) in pyridine (200 ml.) is treated with a solution of γ-carbomethoxybutyryl chloride (35 ml.) in pyridine (500 ml.). The mixture is thoroughly stirred and allowed to stand for 4 days. It is then poured into water (1 liter) and the aqueous mixture extracted with ether (5 × 300 ml.). The combined ethereal extracts are dried over magnesium sulfate and then evaporated. The residue is recrystallized repeatedly from methanol-water to a constant melting point.

PREPARATION E

β-Ethyl-N-Carbobenzyloxy-L-Aspartate

Benzyl chloroformate (8 ml.) is added to β-ethyl-L-aspartate (8.2 g.) in water (120 ml.) containing sodium bicarbonate (8.0 g.) and the mixture stirred at 0°–5°C. for 3 hours, and then at room temperature for 2 hours. The mixture is extracted with ether and the aqueous layer phase acidified with dilute hydrochloric acid. The acid solution is extracted with ether, the ether extract dried ($Na_2SO_4$) and evaporated. The residue is recrystallized from carbon tetrachloride.

We claim:
1. A method for the control of peptic ulcers in animals in need of said treatment which comprises administering intraperitoneally or orally to the animals an effective antipeptic ulcer amount of a composition containing a diluent amount of a pharmaceutically-acceptable carrier and, as the essential active ingredient, an effective amount of a compound having the formula

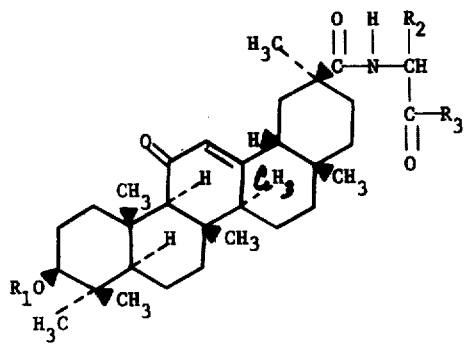

wherein
- $R_1$ is selected from the group consisting of hydrogen, alkanoyl having from two to six carbon atoms and ω-carboxyalkanoyl having a total of from 4 to 5 carbon atoms;
- $R_2$ is selelcted from the group consisting of benzyl, 4-hydroxybenzyl, 3,4-dihydroxybenzyl, and 3,5-dibromo-4-hydroxybenzyl; and
- $R_3$ is selected from the group consisting of hydroxy and alkoxy having from one to four carbon atoms; or a pharmaceutically-acceptable alkali metal salt thereof when the compound has at least one carboxy group.

2. The method of claim 1 wherein the compound is administered at a dose level of from about 150 mg. to about 300 mg. per day.

3. The method of claim 1 wherein the pharmaceutically-acceptable carrier is polyvinylpyrrolidone.

4. The method of claim 2 wherein each of $OR_1$ and $R_3$ is hydroxy.

5. The method of claim 2 wherein $R_1$ is alkanoyl, and $R_3$ is alkoxy.

6. The method of claim 4 wherein the compound is N-[3 β- hydroxy-11-oxo-18 β- olean-12-en-30-oyl]-phenylalanine.

* * * * *